United States Patent
Troesken et al.

(10) Patent No.: US 9,220,574 B2
(45) Date of Patent: Dec. 29, 2015

(54) TISSUE MARKER

(75) Inventors: Volker Troesken, Witten (DE); Laszlo Hasenau, Bochum (DE)

(73) Assignee: amedo smart tracking solutions GmbH, Bochum (DE)

(*) Notice: Subject to any disclaimer, the term of this patent is extended or adjusted under 35 U.S.C. 154(b) by 689 days.

(21) Appl. No.: 12/733,878

(22) PCT Filed: Sep. 24, 2008

(86) PCT No.: PCT/EP2008/008071
§ 371 (c)(1),
(2), (4) Date: Apr. 26, 2010

(87) PCT Pub. No.: WO2009/043512
PCT Pub. Date: Apr. 9, 2009

(65) Prior Publication Data
US 2010/0305430 A1    Dec. 2, 2010

(30) Foreign Application Priority Data
Sep. 26, 2007  (DE) .......................... 10 2007 046 186

(51) Int. Cl.
*A61B 5/05* (2006.01)
*A61B 19/00* (2006.01)
*A61B 5/00* (2006.01)
*A61B 17/00* (2006.01)

(52) U.S. Cl.
CPC .............. *A61B 19/54* (2013.01); *A61B 5/0031* (2013.01); *A61B 2017/00004* (2013.01); *A61B 2019/448* (2013.01); *A61B 2019/547* (2013.01)

(58) Field of Classification Search
CPC ..................... A61B 19/54; A61B 2017/00004; A61B 2019/448; A61B 2019/547; A61B 5/0031

USPC ................. 324/200–243, 301, 302, 306–309, 324/318–322, 637–648; 600/407, 424, 431
See application file for complete search history.

(56) References Cited

U.S. PATENT DOCUMENTS

| 5,221,269 A | 6/1993 | Miller et al. |
| 5,325,873 A | 7/1994 | Hirschi et al. |
| 6,076,007 A * | 6/2000 | England et al. ............... 600/424 |

(Continued)

FOREIGN PATENT DOCUMENTS

| EP | 1 321 097 | 6/2003 |
| WO | WO 2007/087447 | 8/2007 |
| WO | WO 2007/117478 | 10/2007 |

OTHER PUBLICATIONS

International Search Report.

*Primary Examiner* — Mark Remaly
(74) *Attorney, Agent, or Firm* — Collard & Roe, P.C.

(57) ABSTRACT

The invention relates to a tissue marker (1, 1') for marking a lesion (16) in the body tissue (6). The invention is characterized in that the tissue marker (1, 1') comprises a transponder (2). The transponder (2) can be activated by electromagnetic radiation (8) in such a manner that the transponder (2) emits a localization signal (9) in the form of electromagnetic radiation by means of which the position of the tissue marker (1, 1') in the body tissue (6) can be detected. The invention further relates to a system for determining the position of such a tissue marker (1, 1') and to the use of an RFID tag as a tissue marker (1, 1') for marking a lesion (16) in the body tissue. According to an advantageous embodiment of the invention, the tissue marker (1, 1') is biodegradable.

15 Claims, 2 Drawing Sheets

(56) References Cited

U.S. PATENT DOCUMENTS

Figure 1:
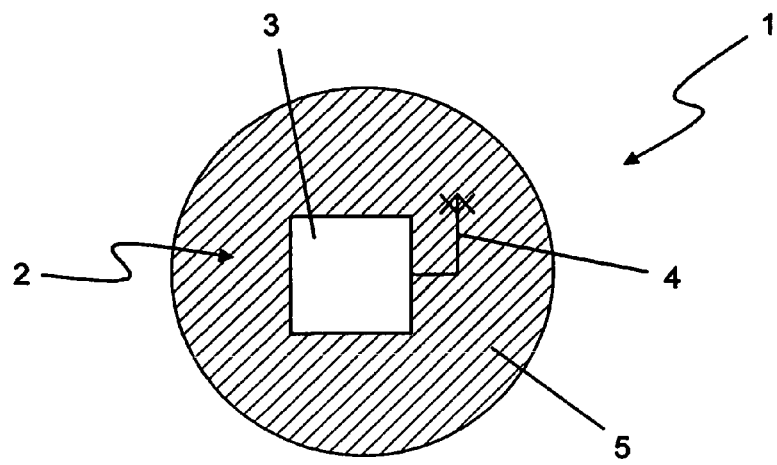

| | | |
|---|---|---|
| 7,026,941 B1 | 4/2006 | Anderson |
| 7,135,978 B2 | 11/2006 | Gisselberg et al. |
| 7,492,326 B1 * | 2/2009 | Bodlovic et al. ............. 343/873 |
| 2002/0083951 A1 | 7/2002 | Stegmaier et al. |
| 2003/0052785 A1 | 3/2003 | Gisselberg et al. |
| 2005/0101946 A1 | 5/2005 | Govari et al. |
| 2005/0195084 A1 | 9/2005 | Dimmer et al. |
| 2007/0106152 A1 | 5/2007 | Kantrowitz et al. |

* cited by examiner

TISSUE MARKER

CROSS REFERENCE TO RELATED APPLICATIONS

This application is the National Stage of PCT/EP2008/008071 filed on Sep. 24, 2008 which claims priority under 35 U.S.C. §119 of German Application No. 10 2007 046 186.2 filed on Sep. 26, 2007. The international application under PCT article 21(2) was not published in English.

The invention relates to a tissue marker for marking a lesion in body tissue.

In medicine, operations for removing tissue samples from the body tissue are frequently carried out, particularly in the diagnosis and treatment of patients with tumors, pre-malignant states, or other locally limited illnesses. Typically, a biopsy is carried out if a physician determines, by means of known techniques (palpation, X-ray, MRI, ultrasound, etc.) that there is a suspicion of disease, in order to determine whether the cells in the region of the lesion found are cancer-like. The biopsy can be an open biopsy or one that is performed in percutaneous manner. In the case of an open biopsy, tissue mass is removed in the region of the lesion, in whole or in part. In the case of the biopsy carried out in percutaneous manner, which is usually carried out with a needle-shaped instrument, small amounts of tissue, if necessary only individual cells, are removed for pathological examination. In all cases, it is important for precise implementation of the operation to be able to localize the location of the lesion, in other words the position of the center of the lesion, as well as the edges of the lesion, as precisely as possible. Precise recognition of the edges of a lesion is important in order to guarantee that the entire lesion is removed during a corresponding operation.

Various techniques for marking and localizing lesions in body tissue are known from the state of the art.

In practice, wire guides are frequently used, as they are described in U.S. Pat. No. 5,221,269. Such wire guides are particularly used to localize lesions in the breast. The wire guide comprises a guide wire that has a helix-shaped coil configuration at its distal end. The guide wire is introduced into the breast by means of a hollow needle, and guided to the lesion location under observation by means of an imaging system. There, the helix-shaped coil at the distal end of the guide wire is anchored in the body tissue. Finally, the hollow needle is removed from the guide wire, which remains anchored in position in the tissue in the region of the lesion. The wire serves to guide a physician to the lesion location during a subsequent operation. The guide wire remains in the tissue and is only removed after the treatment has been completed.

Furthermore, so-called active tissue markers are known from the state of the art. Such a tissue marker is described, for example, in U.S. Pat. No. 7,135,978 B2. The tissue marker consists of a coil that is an integral part of a high-frequency resonance circuit. The coil is implanted in the body, at the proper location, to mark a lesion in the body tissue. The tissue marker can be localized in wireless manner using the electromagnetic field emitted by the high-frequency resonance circuit, in response to corresponding excitation. This method of tissue marking also has the disadvantage that it remains in the body tissue until completion of the therapy, in each instance, and afterwards must be removed by means of a separate operation. This puts stress on the patient.

Against this background, it is the task of the invention to make available an improved tissue marker. In particular, a tissue marker is supposed to be created, which allows reliable localization of a lesion in the body tissue, whereby the patient is supposed to experience as little stress as possible as the result of the tissue marker.

The invention accomplishes this task in that the tissue marker comprises a transponder, whereby the transponder can be activated by means of electromagnetic radiation, specifically in such a manner that the transponder emits a localization signal, on the basis of which the position of the tissue marker in the body tissue can be determined, as electromagnetic radiation.

The basic idea of the invention is the use of a transponder of a known type as a tissue marker for marking a lesion in body tissue.

An RFID tag is particularly well suited as a tissue marker. RFID is known to be a method for contact-free identification and localization. An RFID system consists of a transponder that is situated on the object to be identified and identifies it, and a reader for reading the transponder ID. An RFID transponder (also called an RFID tag) usually comprises an antenna and an integrated electronic circuit, having an analog part and a digital part. The analog part (transceiver) serves for reception and transmission of electromagnetic radiation. The digital circuit has a data memory in which identification data of the transponder can be stored. In the case of more complex RFID transponders, the digital part of the circuit has a Von Neumann architecture. The high-frequency electromagnetic field generated by the reader is received by way of the antenna of the RFID transponder. In the antenna, an induction current occurs as soon as it is in the electromagnetic field of the reader, by means of which current the transponder is activated. The transponder activated in this manner receives commands from the reader by way of the electromagnetic field. The transponder generates a response signal that contains the data requested by the reader. According to the invention, the response signal is the localization signal, on the basis of which the position of the tissue marker in the body tissue is determined.

The use of an RFID transponder as a tissue marker, according to the invention, therefore has the advantage that the tissue marker can be implanted into the body tissue in its entirety, without any guide wire that penetrates the skin permanently remaining in the body, as is the case with the known wire guides.

RFID tags are particularly well suited as tissue markers, since they have a very small construction size. With today's technology, it is possible to produce miniaturized RFID transponders that are only the size of a grain of dust. RFID transponders having a size of 0.05×0.05 mm are known. Such transponders work at very high frequencies, in the range of 1 gigahertz and more. Such a miniaturized RFID transponder can easily remain in body tissue. Operative removal after completion of therapy is not required. Also, the very small RFID transponders can very easily be implanted at the desired location in the body tissue. In the simplest case, this takes place by means of a hollow needle having a small diameter, with monitoring by means of an imaging device.

It is practical if the transponder of the tissue marker according to the invention is configured as a passive transponder, whereby the power supply of the circuit takes place by means of the induction current generated in the antenna during reception of electromagnetic radiation. The small construction size of passive transponders is advantageous, since these make do without their own active energy supply, for example in the form of a battery. The energy that the transponder needs to emit the localization signal is made available by the electromagnetic radiation by means of which activation of the transponder takes place. It is practical if the transponder has a capacitor for supplying power to its integrated circuit, which capacitor is charged by means of the induction current generated in the antenna. Since the permanent energy supply is guaranteed by means of the capacitor, the antenna of the transponder can be dimensioned to be very small, and this in turn is advantageous for use of the transponder as a tissue marker.

According to a practical further development of the tissue marker according to the invention, the transponder is connected with at least one sensor element, whereby the transponder emits a sensor signal of the sensor element as electromagnetic radiation. Accordingly, the transponder is not only used for marking a lesion in the body tissue, but also for transmitting sensor signals that are recorded at the corresponding lesion location. The transponder is connected with corresponding sensor elements, for example a temperature sensor, a pressure sensor, or a pH sensor. The transponder transmits the sensor signal in wireless manner, as an analog or digital signal.

A particularly advantageous embodiment of the tissue marker according to the invention results from the fact that the tissue marker is biodegradable. If the tissue marker is biodegradable, an operation to remove it after completion of therapy for which the tissue marker is required can be eliminated entirely, specifically independent of the size of the tissue marker. Even a tissue marker having large dimensions can be used if the tissue marker is biodegradable. It is possible to produce all the components of the tissue marker, including the transponder, from biodegradable materials, and to configure the surfaces of all the parts of the tissue marker in such a manner that biodegradability is guaranteed. The integrated circuit of the transponder consists essentially of silicon, which is both biodegradable and biocompatible. Known biodegradable and biocompatible materials can easily be selected for the antenna and, if necessary, for other components of the tissue marker. It is particularly practical to embed the tissue marker according to the invention in a biodegradable sheath, whereby the biodegradation time can be predetermined by the thickness and/or the composition of the sheath. In this way, the biodegradation time can be adapted to the duration of the therapy for which the tissue marker is used. Different polymer, ceramic, and metallic materials that are known to be biodegradable and biocompatible are suitable as sheaths for the tissue marker according to the invention.

Using today's technology, it is possible to produce RFID tags using the printing method. RFID tags printed in this way are well suited as tissue markers according to the invention. It is possible, for example, to print an RFID tag onto a substrate of biodegradable material, as a tissue marker.

As has been mentioned above, it is important for precise implementation of an operation to be able to localize the location of the lesion, in other words the position of the center of the lesion, as well as the edges of the lesion, as precisely as possible. For this purpose, a plurality of tissue markers according to the invention can advantageously be used. For example, a single tissue marker can be used to mark the center of a lesion, while other tissue markers are placed at the edge of the lesion, in order to make the precise delimitation of the lesion recognizable to the surgeon. The individual RFID tags of the tissue marker can store medical data with regard to the lesion to be marked in their electronic data memory, so that the physician, when querying the RFID tag, in each instance, obtains additional data about the lesion, which are important for performing the operation. For example, data concerning the size of the lesion can be contained in the data memory of an RFID tag that is used as a tissue marker for marking the center of a lesion. In this manner, the physician obtains information about the amount of tissue to be removed, in order to guarantee that the entire lesion is removed. Since the individual RFID tags can be differentiated on the basis of their individual identification data, these can be utilized to essentially mark "path points" for an operation to be performed. The physician can move from one of these "path points" to another, in a previously established sequence, when performing the operation.

A system for determining the position of a tissue marker according to the invention in body tissue comprises a transmission unit for emitting electromagnetic radiation for activation of the transponder of the tissue marker, a reception unit for receiving the localization signal emitted by the transponder, and an evaluation unit for evaluating the localization signal. The transmission unit, the reception unit, and the evaluation unit together form a reader, as is fundamentally usual for reading RFID tags, whereby the evaluation unit is expanded to include functions for determining the position of the tissue marker on the basis of the localization signal. It is possible to use multiple reception units that receive the signal emitted by the transponder. A conclusion concerning the distance of the transponder from the reception unit can be drawn from the field intensity of the localization signal at the location of the reception unit, in each instance. If the distances of the transponder from the different reception units, which are situated at defined locations in space, are known, the evaluation unit, in turn, can calculate the precise position of the transponder and thus of the tissue marker in the body tissue from this information.

It is problematical that the field intensity of the localization signal is weakened by the body tissue. Because of its electrical properties, the body tissue partly absorbs electromagnetic radiation emitted by the transponder. For this reason, a position determination based on the field intensity of the localization signal is not always possible with sufficient accuracy, under some circumstances. To solve this problem, the evaluation unit can be set up for determining the position of the tissue marker on the basis of the phasing of the electromagnetic radiation of the localization signal at the location of the reception unit, in each instance. If the frequency of the localization signal is suitably selected, the influence of the electrical properties of the body tissue on the phase of the localization signal is low. In this connection, the transponder should be set up in such a manner that it emits the localization signal in coherent manner, in other words with a defined and constant phasing.

If the position determination, as described above, takes place on the basis of the phasing of the electromagnetic radiation of the localization signal, it must be noted that a clear assignment of a phase value to a position in space is only possible within a distance that is smaller than the wavelength of the localization signal. At greater distances, it is additionally necessary to determine the number of zero passes of the electromagnetic waves between the transponder and the reception unit, in each instance.

In order to achieve the greatest possible precision in the position determination, it can be practical to configure the transponder and the related reception units in such a manner that they work at two or more different frequencies. In this way, a stepped localization method for successively increasing the accuracy in the position determination can be implemented. By generating the localization signal at low frequencies and correspondingly great wavelengths, first a rough but clear determination of the position can take place. To increase the precision, a switch is then made to a higher frequency, or the frequency of the localization signal is successively increased further. At higher frequencies, the demands on the resolution in determining the phasing to achieve a specific spatial resolution become less. In the successive increase in the frequency, the number of zero passes to determine the precise distance between transponder and reception unit can be determined. For the most precise position determination possible, a change in frequency in both directions, in other words from low to high frequencies, but also from high to low frequencies, is possible. It can be necessary to provide two or more antennas, depending on the frequency ranges that have to be covered for the position determination, with which antennas the circuit of the transponder is connected, whereby each of the antennas is assigned to a specific frequency range, in each instance. It is also possible to use tissue markers that comprise separate transponders, in each instance, which work at different frequencies.

According to a practical further development of the system, an aiming device for determining the position of a medical instrument relative to the position of the tissue marker is provided. The aiming device determines the position and/or orientation of a medical instrument used to carry out an operation, relative to the tissue marker according to the invention. In this manner, the aiming device can indicate to a physician in what direction he must guide the instrument in order to reach the position of the tissue marker, and thus the lesion location, with the instrument (or its tip). At the same time, the aiming device can indicate to the physician the distance of the instrument from the tissue marker, so that the physician receives information about the path distance by which the instrument must be advanced in order to reach the lesion location. The display of the aiming device can comprise an arrow representation, for example, whereby the arrow indicates to the physician in what direction he must move the instrument. Also possible is an indication by means of an acoustical signal or a vibration signal emitter. The aiming device can be affixed directly to the medical instrument, or it can be possible to affix it. It is equally good if the aiming device is separate from the medical instrument. In order to determine the position and/or orientation of the medical instrument relative to the position of the tissue marker, the medical instrument can, in turn, be provided with one or more RFID tags, whose position is determined in the manner described above. It is possible to affix an RFID tag on the medical instrument by means of a printing process, in known manner. Alternatively, the transmission and/or reception unit of the system according to the invention can be connected with the medical instrument, in order to thereby detect the relative position of instrument and tissue marker. It is practical if the transmission and/or reception unit of the system have a directional characteristic, in order to detect the direction of the localization signal emitted by the tissue marker with reference to the orientation of the medical instrument.

When using a tissue marker according to the invention, the problem can occur that the marker "migrates" in the body tissue, so that the location of the lesion no longer agrees with the location of the tissue marker. In order to check this and to be able to exclude this possibility, it is practical to implant two or more tissue markers in a defined geometrical configuration. If one finds, when checking the positions of the individual tissue markers, that their relative placement in the body has changed as compared with the original configuration, this indicates "migration" of at least one of the markers. In this case, the marker must be qualified as no longer usable. It is considered extremely unlikely that several tissue markers "migrate" in identical manner and maintain their relative configuration when doing so.

The tissue marker according to the invention is suitable as a focus marker in radiotherapy. The marked lesion can automatically be brought into the beam path, i.e. into the focus of the radiotherapy radiation source, after the position of the tissue marker in the body tissue has been determined. Likewise, the radiation source, i.e. its collimation optics can automatically be aimed at the lesion location. It is also very well possible to automatically set the collimator of the radiation source for the target contour, in accordance with the delimitations of the lesion (which has preferably been marked with multiple tissue markers according to the invention).

Exemplary embodiments of the invention will be explained in greater detail below, using the figures.

Figure 2:
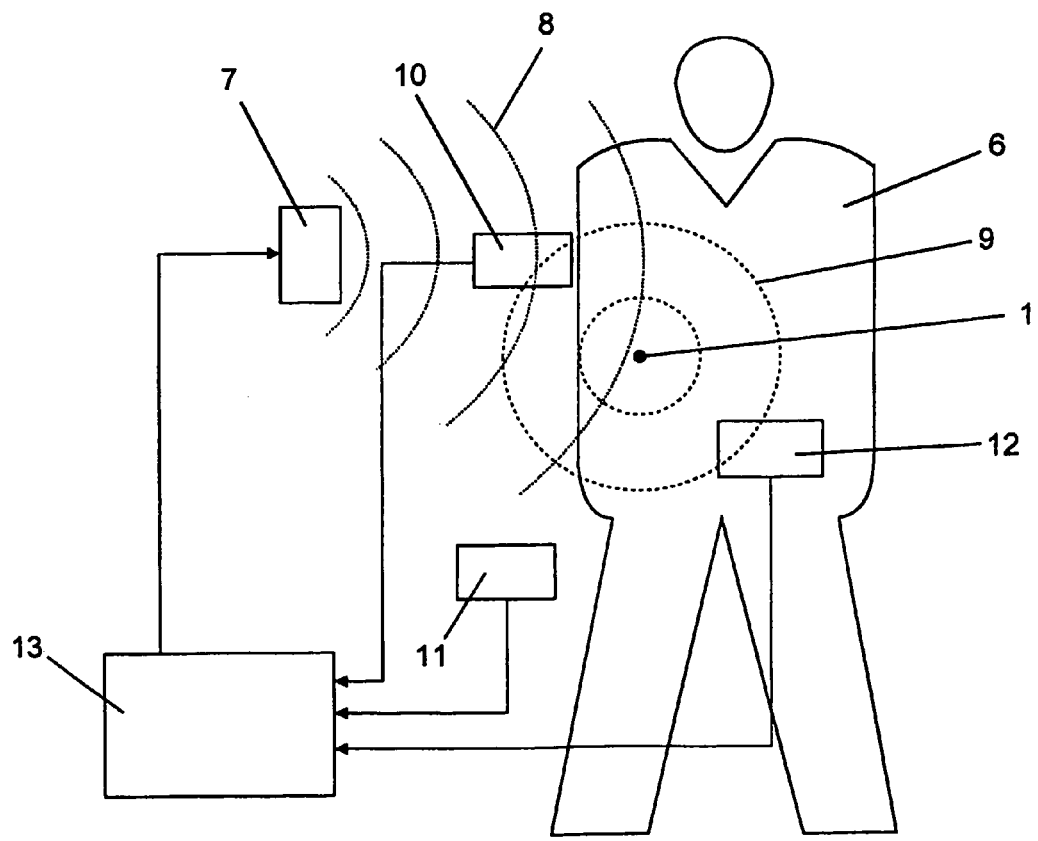
Figure 3:
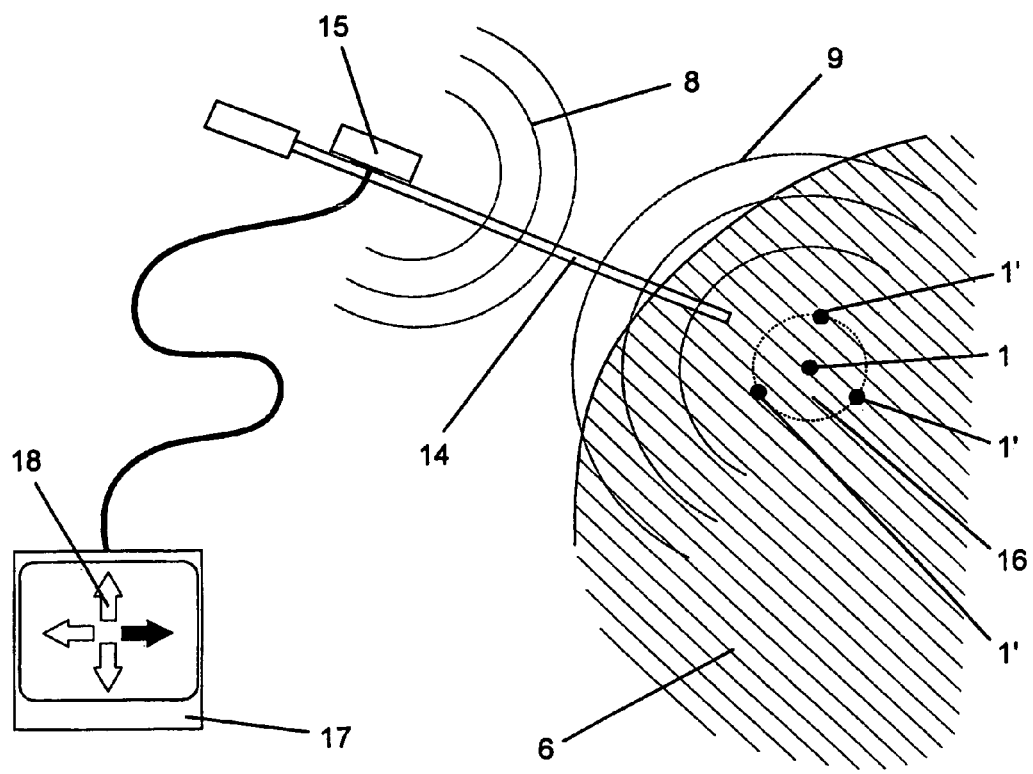

These show:

FIG. 1 schematic representation of a tissue marker according to the invention;

FIG. 2 system according to the invention for determining the position of a tissue marker;

FIG. 3 medical instrument with an aiming device according to the invention.

The tissue marker shown in FIG. 1 is designated, as a whole with the reference number 1. This marker comprises a transponder 2, which consists of an integrated electronic circuit 3 and an antenna 4. The tissue marker 1 is configured to be biodegradable. In order to be able to determine the biodegradation time in targeted manner, the tissue marker 1 has a biodegradable sheath 5 that encloses the transponder 2. The biodegradation time is pre-determined by the thickness, the composition, and the surface structure of the sheath 5. By means of suitable surface structuring of the sheath 5, "migration" of the tissue marker in the body tissue can furthermore be prevented. A rough or porous surface structuring promotes biodegradability, and, at the same time, brings about growth of tissue into the sheath, so that the tissue marker 1 is securely fixed in place at the lesion location to be marked.

The system shown in FIG. 2 serves for determining the position of a tissue marker 1 in the body tissue 6 of a patient. The system comprises a transmission unit 7, which emits electromagnetic radiation 8. The radiation 8 is received by the transponder of the tissue marker 1. The transponder is excited by the received radiation 8, so that it, in turn, emits a localization signal as a high-frequency electromagnetic radiation 9. The localization signal 9 emitted by the transponder of the tissue marker 1 is received by three reception units 10, 11, and 12 that are situated at defined positions in space. The reception units 10, 11, and 12 are connected with an evaluation unit 13, which calculates the position of the tissue marker 1 on the basis of the intensity and on the basis of the phasing of the electromagnetic radiation of the localization signal 9 at the location of the reception units 10, 11, and 12, in each instance.

FIG. 3 shows a medical instrument 14 with an aiming device 15. The aiming device 15 serves for determining the position of the medical instrument 14 relative to the position of tissue markers 1 and 1', respectively, which are situated in the body tissue 6. The tissue marker 1 serves to mark the center of a lesion 16. The tissue markers 1' are disposed along the edge of the lesion 16, in order to make the size of the lesion 16 recognizable. The aiming device 15 comprises the transmission unit 7 as well as a reception unit 10 (see FIG. 2). The aiming device 15 emits electromagnetic radiation 8, by means of which the transponders of the tissue markers 1 or 1', respectively, are activated and excited to emit a localization signal 9. Using the localization signal 9 received by way of the aiming device 15, the latter determines the relative position and/or orientation of the instrument 14 relative to the tissue markers 1 and 1', respectively. The individual tissue markers 1 and 1' can be differentiated on the basis of the identification data of the individual transponders. When performing an operation, the physician can select a specific tissue marker 1 or 1', respectively, to which he would like to guide the instrument 14. The aiming device 15 is connected with a display 17 that indicates the guidance direction or the orientation of the instrument 14 to the physician, so that it is guided to the position of the selected tissue marker 1 or 1'. For this purpose, the display 17 shows arrows 18 that give the physician clear information for how to orient the instrument 14 correctly.

The invention claimed is:

1. Tissue marker for marking a lesion in body tissue, wherein the tissue marker comprises a transponder, whereby the transponder can be activated via electromagnetic radiation, specifically in such a manner that the transponder emits a localization signal to determine the position of the tissue marker in the body tissue as electromagnetic radiation, wherein the transponder is arranged to emit the localization signal in a coherent manner, with a defined and constant phasing, in order to assign a phase value to a position in space, and wherein the tissue marker is biodegradable and has a biodegradable sheath that encloses the transponder, whereby the biodegradation time can be pre-determined by the thickness and/or the composition of the sheath.

2. Tissue marker according to claim 1, wherein the transponder has an integrated electronic circuit and an antenna connected with the latter, for reception and transmission of electromagnetic radiation.

3. Tissue marker according to claim 2, wherein the transponder is configured as a passive transponder, whereby the power supply of the circuit takes place via the induction current generated in the antenna during reception of electromagnetic radiation.

4. Tissue marker according to claim 1, wherein the tissue marker has a sensor element connected with the transponder, whereby the transponder emits a sensor signal of the sensor element as electromagnetic radiation.

5. Tissue marker according to claim 1, wherein the transponder is a radio frequency identification (RFID) tag.

6. Tissue marker according to claim 5, wherein medical data with regard to the lesion to be marked are stored or can be stored in an electronic data memory of the RFID tag.

7. System for determining the position of a tissue marker according to claim 1 in body tissue, the system comprising the tissue marker according to claim 1 and further comprising a transmitter for emitting electromagnetic radiation for activation of the transponder of the tissue marker, a receiver for receiving the localization signal emitted by the transponder, and having a processor for evaluating the localization signal, wherein the processor is set up for determining the position of the tissue marker by determining the phasing of the electromagnetic radiation of the localization signal at the location of the reception unit, in order to assign a phase value to a position in space.

8. System according to claim 7, further comprising an aiming device for determining the position and/or orientation of a medical instrument relative to the position of the tissue marker, the aiming device comprising at least one of an aiming device transmitter affixed to the medical instrument and an aiming device receiver affixed to the medical instrument.

9. System according to claim 8, wherein the aiming device has a display that indicates the guidance direction or the orientation of the medical instrument to the person guiding the medical instrument, so that the medical instrument is guided to the position of the tissue marker.

10. System according to claim 7, wherein at least one of the transmitter and the receiver has a directional characteristic.

11. System according to claim 7, wherein the tissue marker can be identified via the processor through an identification signal emitted by the transponder of the tissue marker and received by way of the receiver.

12. Method for determining the position of a tissue marker in body tissue, wherein an electromagnetic signal is emitted via a transmitter, which electromagnetic signal is received by a transponder of the tissue marker, whereupon the transponder emits a localization signal that is received by way of a receiver, whereby the position of the tissue marker is determined via a processor that is connected with the receiver, from the localization signal, wherein the position is determined by determining the phasing of the electromagnetic radiation of the localization signal at the location of the receiver, in order to assign a phase value to a position in space, wherein the tissue marker is biodegradable and has a biodegradable sheath that encloses the transponder, whereby the biodegradation time can be pre-determined by the thickness and/or the composition of the sheath, and wherein the tissue marker biodegrades in the body according to the biodegradation time.

13. Method according to claim 12, further comprising an aiming device for determining the position or orientation of a medical instrument relative to the position of the tissue marker, wherein the aiming device comprises at least one of an aiming device transmitter affixed to the medical instrument and an aiming device receiver affixed to the medical instrument, whereby via the aiming device the guidance direction and/or the orientation of the medical instrument are indicated to the person guiding the medical instrument, so that the medical instrument is guided to the position of the tissue marker.

14. Method according to claim 12, wherein the marked lesion is brought into the beam path of a radiation-therapy radiation source, and/or the radiation of the radiation source is oriented toward the lesion location, in accordance with the determination of the position of the tissue marker.

15. Method according to claim 12, wherein the transponder emits the localization signal in a coherent manner, with a defined and constant phasing.

* * * * *